United States Patent [19]

Kühle et al.

[11] Patent Number: 4,529,735
[45] Date of Patent: Jul. 16, 1985

[54] N-SULPHENYLATED PYRANOPYRAZOLE DERIVATIVE PLANT PROTECTION AGENTS

[75] Inventors: Engelbert Kühle, Bergisch-Gladbach; Hartmut Stegelmeier, Hilden; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 610,361

[22] Filed: May 15, 1984

[30] Foreign Application Priority Data

May 25, 1983 [DE] Fed. Rep. of Germany ....... 3318876

[51] Int. Cl.³ .................. A01N 43/56; C07D 491/52; C07D 491/153; C07D 495/14
[52] U.S. Cl. ..................... 514/407; 548/370
[58] Field of Search ................... 548/370; 424/273 P

[56] References Cited

U.S. PATENT DOCUMENTS 3,624,102 11/1971 Brown et al. ................. 548/370

FOREIGN PATENT DOCUMENTS 157396 12/1975 Japan .................. 548/370

Primary Examiner—Richard A. Schwartz
Assistant Examiner—Kurt G. Briscoe
Attorney, Agent, or Firm—Sprung, Horn, Kramer & Woods

[57] ABSTRACT

N-Sulphenylated pyranopyrazole derivatives of the formula

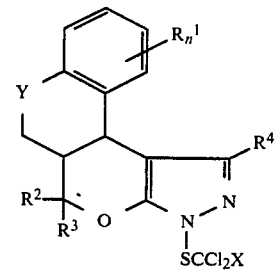

in which
  $R^1$ is halogen, alkyl, alkoxy, alkylthio, halogenoalkyl, dialkylamino, nitro or cyano,
  $R^2$ and $R^3$ each independently is hydrogen, alkyl or optionally substituted phenyl,
  $R^4$ is cyano, alkyl, alkoxycarbonyl or optionally substituted phenyl,
  X is halogen,
  Y is oxygen, sulphur or the methylene group, and
  n is an integer from 0 to 3,
which possess fungicidal activity.

12 Claims, No Drawings

N-SULPHENYLATED PYRANOPYRAZOLE DERIVATIVE PLANT PROTECTION AGENTS

The invention relates to new N-sulphenylated pyranopyrazole derivatives, a process for their preparation and their use as agents for controlling pests.

It is already known that, in addition to a number of other substance classes, certain heterocycles, such as, for example, N-trichloromethylthiotetrahydrophthalimide, also have fungicidal properties (compare R. Wegler "Chemie der Pflanzenschutz-und Schädlingsbekämpfungsmittel" (The Chemistry of Plant-Protection Agents and Agents for controlling pests) Volume 2, page 108, Springer Verlag, Berlin/Heidelberg/New York 1970).

However, in certain circumstances, especially when the amounts and concentrations applied are low, the efficacy of these compounds is not always completely satisfactory.

New N-sulphenylated pyranopyrazole derivatives of the general formula (I)

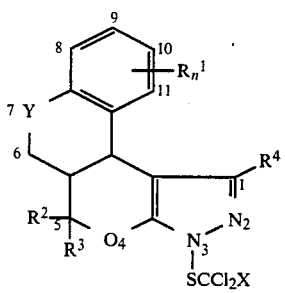

in which

R$^1$ represents halogen, alkyl, alkoxy, alkylthio, halogenoalkyl, dialkylamino, nitro or cyano, R$^2$ and R$^3$ can be identical or different and represent hydrogen, alkyl or optionally substituted phenyl, R$^4$ represents cyano, alkyl, alkoxycarbonyl or optionally substituted phenyl, x represents halogen, y represents oxygen, sulphur or the methylene group, and n represents an integer from 0 to 3, have been found.

In addition, it has been found that the new N-sulphenylated pyranopyrazole derivatives of the general formula (I)

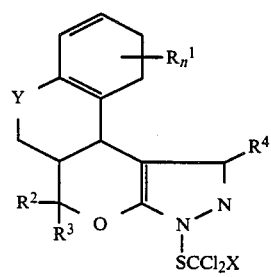

in which

R$^1$ represents halogen, alkyl, alkoxy, alkylthio, halogenoalkyl, dialkylamino, nitro or cyano, R$^2$ and R$^3$ can be identical or different and represent hydrogen, alkyl or optionally substituted phenyl, R$^4$ represents cyano, alkyl, alkoxycarbonyl or optionally substituted phenyl, X represents halogen, Y represents oxygen, sulphur or the methylene group, and n represents an integer from 0 to 3, are obtained by reacting, in the present of an acid-binding agent and, where appropriate, in the presence of a diluent, pyranopyrazoles of the general formula (II)

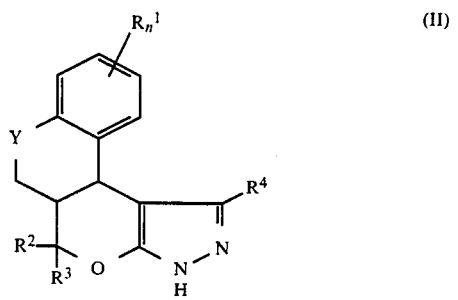

in which R$^1$, R$^2$, R$^3$, R$^4$, Y and n have the meaning indicated above, with a sulphenyl chloride of the general formula (III)

$$XCL_2CSCL \qquad (III)$$

in which X has the meaning indicated above.

The new N-sulphenylated pyranopyrazole derivatives of the general formula (I) are distinguished by great efficacy as agents for controlling pests, especially by their excellent fungicidal activity.

Thus, the substances according to the invention are an enrichment of technology.

The N-sulphenylated pyranopyrazole derivatives according to the invention are generally defined by formula (I).

The alkyl radicals in R$^1$, R$^2$, R$^3$ and R$^4$ and the alkoxy moiety in the alkoxycarbonyl radical in R$^4$ can be straight-chain or branched and they each preferably contain 1 to 6, especially 1 to 4, and particularly preferably 1 or 2, carbon atoms. The alkyl moieties in the alkoxy, alkylthio, halogenoalkyl and dialkylamino radicals in R$^1$ can be straight-chain or branched and they each preferably contain 1 to 4, especially 1 to 3 and particularly preferably 1 or 2, carbon atoms. The halogenoalkyl moiety in the mentioned radical preferably contains 1 to 7, especially 1 to 5, identical or different halogen atoms, such as fluorine, chlorine, bromine or iodine, preferably fluorine and/or chlorine.

The following radicals may be listed as examples of the groups mentioned: methyl, ethyl, n-propyl, i-propyl, n-butyl, i-butyl, sec.-butyl, tert,-butyl, methoxy, ethoxy, n-propoxy, i-propoxy, n-butoxy, i-butoxy, sce-butoxy, tert.-butoxy, methylthio, ethylthio, n-n-propylthio, i-propylthio, n-butylthio, i-butylhtio, sec.-butylthio, tert.-butylthio, trifluoromethyl, trichloromethyl, dichlorofluoromethyl, chlorodifluoromethyl, difluoromethyl, trifluoroethyl, trichloroethyl, dichlorofluoroethyl, chlorodifluoroethyl, difluoroethyl, dimethylamino, diethylamino, di-n-propylamino, methoxycarbonyl, ethoxycarbonyl, n-propoxycarbonyl and iso-propoxycarbonyl. Unless otherwise indicated, halogen denotes fluorine, chlorine, bromine and iodine, preferably chlorine, bromine and fluorine.

Phenyl substituents in $R^2$, $R^3$ and $R^4$ which may be mentioned are halogen and/or alkyl with the meaning of these radicals indicated above.

Those compounds of the formula (I) in which $R^1$ represents halogen, cyano, nitro, straight-chain or branched alkyl having up to 4 carbon atoms, alkoxy, alkylthio or dialkylamino having 1 or 2 carbon atoms in the particular alkyl moieties or halogenoalkyl having 1 or 2 carbon atoms and up to 5 identical or different halogen atoms, such as monohalogenoalkyl, dihalogenoalkyl, trihalogenoalkyl, tetrahalogenoalkyl or pentahalogenoalkyl, and $R^2$ and $R^3$, which can be identical or different, represent hydrogen, straight-chain or branched alkyl having up to 4 carbon atoms or phenyl which is optionally monosubstituted to pentasubstituted, identically or differently, by halogen or alkyl having up to 4 carbon atoms, $R^4$ represents cyano, straight-chain or branched alkyl or alkoxycarbonyl each having up to 4 carbon atoms in the alkyl moiety, or phenyl which is optionally monosubstituted to pentasubstituted, identically or differently, by halogen or alkyl having up to 4 carbon atoms, X represents chlorine or fluorine, Y represents oxygen, sulphur or the methylene group, and n represents an integer from 0 to 3 are preferred.

Those compounds of the formula (I) in which $R^1$ represents fluorine, chlorine, bromine, cyano, nitro, methyl, methoxy, methylthio, dimethylamino or trifluoromethyl, and $R^2$ and $R^3$, which can be identical or different, represent hydrogen, methyl or phenyl which is optionally monosubstituted to trisubstituted, identically or differently, by chlorine or methyl, $R^4$ represents methyl, ethyl, n- and i-propyl, t-butyl, cyano, methoxycarbonyl, ethoxycarbonyl and phenyl which is optionally monosubstituted to trisubstituted, identically or differently, by chlorine or methyl, X represents chlorine or fluorine Y represents oxygen, sulphur or the methylene group, and n represents an integer from 0 to 2 are very particularly preferred.

Apart from the compounds mentioned in the preparation examples, the following compounds of the general formula (I) may be specifically mentioned:

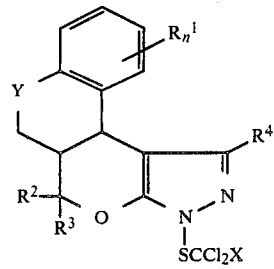

(I)

| $R^2$ | $R^3$ | $R^4$ | $R^1$ | Y | n | X |
|---|---|---|---|---|---|---|
| CH$_3$ | CH$_3$ | CH$_3$ | — | —CH$_2$— | 0 | F |
| CH$_3$ | CH$_3$ | CH$_3$ | 8,11-Cl$_2$ | S | 2 | F |
| CH$_3$ | CH$_3$ | CN | — | O | 0 | Cl |
| CH$_3$ | CH$_3$ | CN | — | O | 0 | F |
| CH$_3$ | CH$_3$ | CH$_3$ | — | S | 0 | F |
| CH$_3$ | CH$_3$ | CH$_3$ | 10-NO$_2$ | —CH$_2$— | 1 | F |
| CH$_3$ | CH$_3$ | CH$_3$ | 8,11-Cl$_2$ | —CH$_2$— | 2 | F |

When, for example, 1,5,5-trimethyl-5a,11b-dihydro-3H,5H,6H,4,7-dioxa-2,3-diazacyclopenta-(c)-phenanthrene and dichlorofluoromethanesulphenyl chloride are used as starting materials, then the course of the reaction in the process according to the invention can be represented by the diagram below:

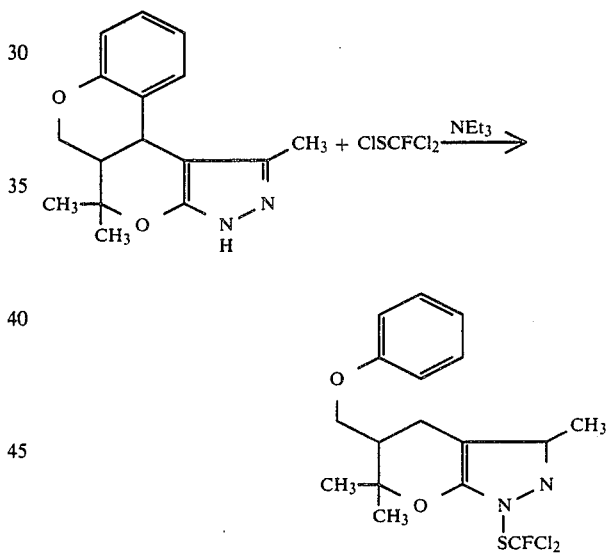

The pyranopyrazoles necessary for carrying out the process according to the invention are generally defined by the formula (II).

Their preparation is carried out according to a process which does not belong to the state of the art, that is to say it has not previously been published, from substituted aromatic aldehydes of the general formula (IV)

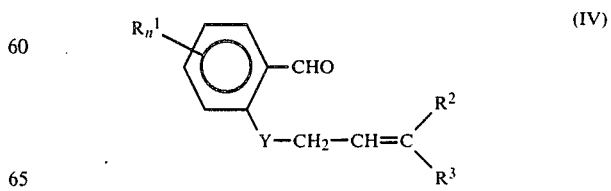

(IV)

in which $R^1$, $R^2$, $R^3$, Y and n have the meaning indicated above, with pyrazolinones of the general formula (V)

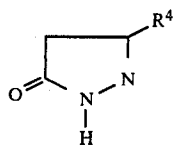

in which R⁴ has the meaning indicated above,
in the presence of a diluent and, where appropriate, in the presence of a catalyst.

The substituted aromatic aldehydes of the formula (IV) are known (compare, for example, "Chem. Pharm. Bull." 27, 2943 (1979) or Belgian Patent Specification 816,463 or Liebigs, Ann. Chem. 401, 21 (1913)).

Likewise, the pyrazolinones of the formula (V) are known (compare, for example, "The Chemistry of Heterocyclic Compounds" Vol 20, Wiley, New York 1964).

The known sulphenyl chlorides which are also required for carrying out the process according to the invention are generally defined by the formula (III).

Specifically, it is possible to employ dichlorofluoromethanesulphenyl and trichloromethanesulphenyl chlorides.

All inert organic solvents are suitable as diluents for carrying out the process. These preferably include hydrocarbons, such as toluene, chlorinated hydrocarbons, such as methylene chloride and chlorobenzene, or ethers, such as dioxane. However, it is also possible to carry out the reaction in an aqueous medium.

Inorganic bases, such as sodium hydroxide and sodium carbonate, or tert. amines, such as pyridine and triethylamine, can be used as the acid-binding agents.

The reaction temperatures can be varied within a relatively wide range. In general, the process is carried out at 0° C. to 100° C., preferably from 20° to 50° C.

The active compounds according to the invention exhibit a powerful microbicidal action and can be employed in practice for combating undesired microorganisms. The active compounds are suitable for use as plant protection agents.

Thus, for example, fungicidal agents are employed in plant protection for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Botrytis species, such as, for example, against the grey mould causative organism (*Botrytis cinerea*). In addition, they can also be used for combating rice diseases, such as, for example, against Pyricularia and Pellicularia sasakii.

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or di tomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared thereform by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The process according to the invention is intended to be illustrated by the preparation examples which follow.

PREPARATION EXAMPLES

Example 1

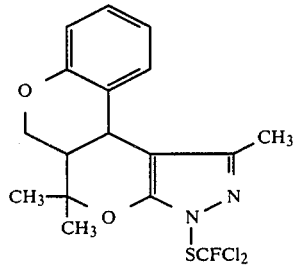

13.6 g (0.05 mol) of 1,5,5-trimethyl-5a,11b-dihydro-3H,5H,6H,4,7-dioxa-2,3-diazacyclopenta-(c)-phenanthrene are vigorously stirred in 100 ml of dioxane with the addition of 6 g (0.06 mol) of triethylamine. 8.5 g (0.05 mol) of dichlorofluoromethanesulphenyl chloride are added dropwise to this at about 20° C.; the temperature rises to about 50° C. during this. The mass of crystals is stirred for about 1 hour, water is added and the reaction product is filtered off with suction. It is washed with methanol and dried at 50° C. 15 g of 1,5,5-trimethyl-3-dichlorofluoromethylthio-5a,11b-dihydro-3H,5H,6H,4,7-dioxa-2,3-diazacyclopenta(c)phenanthrene of melting point 178°–180° C. are obtained.

The following compounds of the formula I can be prepared in an analogous manner:

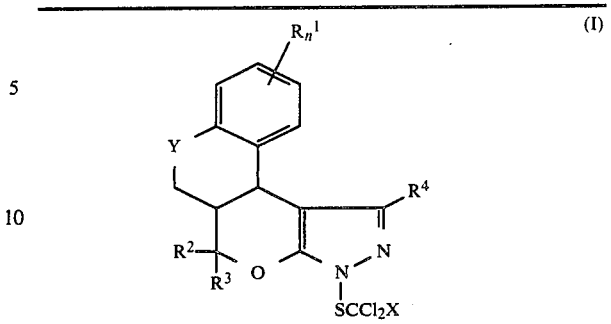

| Ex. No. | X | Y | R¹ | n | R² | R³ | R⁴ | Melting point [°C.] |
|---|---|---|---|---|---|---|---|---|
| 2 | Cl | O | — | 0 | CH₃ | CH₃ | CH₃ | 158 |
| 3 | F | O | 10-Br | 1 | CH₃ | CH₃ | CH₃ | 100 |
| 4 | F | O | 8, 10-Cl₂ | 2 | CH₃ | CH₃ | CH₃ | 112 |
| 5 | F | O | 9-CH₃O | 1 | CH₃ | CH₃ | CH₃ | 95 |
| 6 | F | O | 8-CH₃O | 1 | CH₃ | CH₃ | CH₃ | 137 |
| 7 | F | S | — | 0 | CH₃ | CH₃ | CH₃ | 95–100 |

Use Examples

In the use examples which follow, the compounds detailed below are employed as comparison substances:

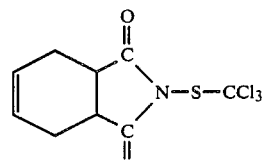

(N—Trichloromethylthiotetrahydrophthalimide)

and

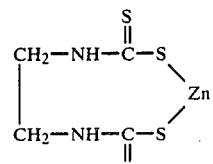

(Zinc ethylenedisbithiocarbamate)

Example A

Botrytis test (bean)/protective

Solvent: 4.7 parts by weight of acetone
Emulsifier: 0.3 parts by weights of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating had dried on, 2 small pieces of agar covered with Botrytis cinerea are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples: 1, 3, 4 and 5.

EXAMPLE B

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 4, 6 and 7.

EXAMPLE C

Pyricularia test (rice)/systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvents, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 5, 6 and 7.

It will be appreciated that the instant specification and examples are set forth by way of illustration and not limitation, and that various modifications and changes may be made without departing from the spirit and scope of the present invention.

We claim:

1. An N-sulphenylated pyranopyrazole derivative of the formula

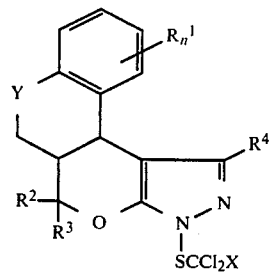

in which
R$^1$ is halogen, alkyl, alkoxy, alkylthio, halogenoalkyl, dialkylamino, nitro or cyano,
R$^2$ and R$^3$ each independently is hydrogen, alkyl or optionally substituted phenyl,
R$^4$ is cyano, alkyl, alkoxycarbonyl or optionally substituted phenyl,
X is halogen,
Y is oxygen, sulphur or the methylene group, and n is an integer from 0 to 3,
the alkyl moieties when present each having up to 6 carbon atoms and the optional substituents on phenyl when present being halogen and/or alkyl having up to 4 carbon atoms.

2. An N-sulphenylated pyranopyrazole derivative according to claim 1,
in which
R$^1$ is halogen, cyano, nitro, alkyl having up to 4 carbon atoms, alkoxy, alkylthio or dialkylamino having 1 or 2 carbon atoms in each alkyl moiety, or monohalogenoalkyl, dihalogenoalkyl, trihalogenoalkyl, tetrahalogenoalkyl or pentahalogenoalkyl, and
R$^2$ and R$^3$, each independently is hydrogen, alkyl having up to 4 carbon atoms or phenyl which is optionally substituted by halogen and/or alkyl having up to 4 carbon atoms,
R$^4$ is alkyl or alkoxycarbonyl each having up to 4 carbon atoms in the alkyl moiety, cyano or phenyl which is optionally substituted by halogen and/or alkyl having up to 4 carbon atoms, and
X is chlorine or fluorine.

3. An N-sulphenylated pyranopyrazole derivative according to claim 1,
in which
R$^1$ is fluorine, chlorine, bromine, cyano, nitro, methyl, methoxy, methylthio, dimethylamino or trifluoromethyl,
R$^2$ and R$^3$ each independently is hydrogen, methyl or phenyl which is optionally monosubstituted to trisubstituted by chlorine and/or methyl,
R$^4$ is methyl, ethyl, n- or i-propyl, t-butyl, cyano, methoxycarbonyl, ethoxycarbonyl or phenyl which is optionally monosubstituted to trisubstituted by chlorine and/or methyl,
X is chlorine or fluorine, and
n is an integer from 0 to 2.

4. A compound according to claim 1, wherein such compound is 1,5,5-trimethyl-3-dichlorofluoromethylthio-5a, 11b-dihydro-3H,5H,6H,4,7-dioxa-2,3-diazacyclopenta(c)phenanthrene of the formula

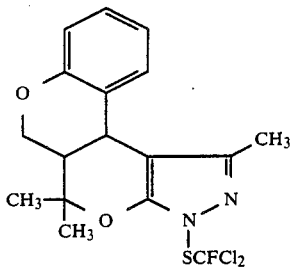

5. A compound according to claim 1, wherein such compound is 10-bromo-1,5,5-trimethyl-3-dichlorofluoromethylthio-5a, 11b-dihydro-3H,5H,6H,4,7-dioxa-2,3-diazacyclopenta(c) phenanthrene of the formula

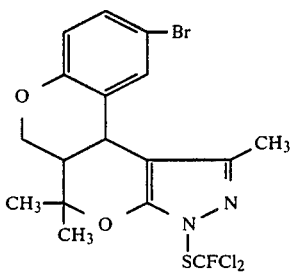

6. A compound according to claim 1, wherein such compound is 8,10-dichloro-1,5,5-trimethyl-3-dichlorofluoromethylthio-5a, 11b-dihydro-3H,5H,6H,4,7-dioxa-2,3-diazacyclopenta(c)phenanthrene of the formula

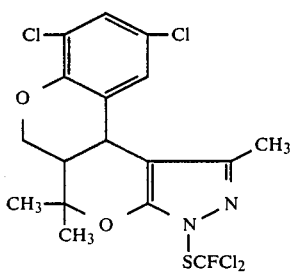

7. A compound according to claim 1, wherein such compound is 9-methoxy-1,5,5-trimethyl-3-dichlorofluoromethylthio-5a, 11b-dihydro-3H,5H,6H,4,7-dioxa-2,3-diazacyclopenta(c)phenanthrene of the formula

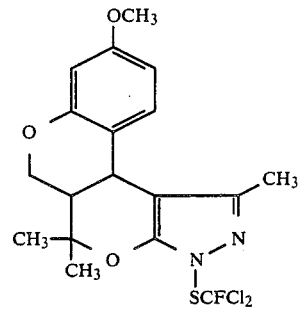

8. A compound according to claim 1, wherein such compound is 8-methoxy-1,5,5-trimethyl-3-dichlorofluoromethylthio-5a, 11b-dihydro-3H,5H,6H,4,7-dioxa-2,3-diazacyclopenta(c)phenanthrene of the formula

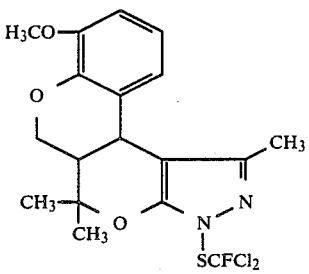

9. A compound to claim 1, wherein such compound is 1,5,5-trimethyl-3-dichlorofluoromethylthio-5a,11b-dihydro-3H,5H,4-oxa-7-thia-2,3,-diazacyclopenta(c)-phenanthrene of the formula

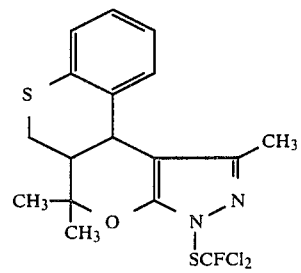

10. A fungicidal composition comprising a fungicidally effective amount of a compound according to claim 1 in admixture with a diluent.

11. A method of combatting fungi which comprises administering to such fungi or to a fungus habitat a fungicidally effective amount of a compound according to claim 1.

12. The method according to claim 11, wherein such compound is 1,5,5-trimethyl-3-dichlorofluoro methylthio-5a, 11b-dihydro-3H,5H,6H,4,7-dioxa-2,3-diazacyclopenta(c)phenanthrene: 10-bromo-1,5,5-trimethyl-3-dichlorofluoromethylthio-5a, 11b-dihydro-3H,5H,6H,4,7-dioxa-2,3,-diazacyclopenta(c)phenanthrene; 8,10-dichlor-1,5,5-trimethyl-3-dichlorofluoromethylthio-5a, 11b-dihydro-3H,5H,6H,4,7-dioxa-2,3-diazacyclopenta(c)phenanthrene; 9-methoxy-1,5,5-trimethyl-3-dichlorofluoromethylthio-5a, 11b-dihydro-3H,5H,6H,4,7-dioxa, 2,3-diazacyclopenta(c)phenanthrene; 8-methoxy-1,5,5-trimethyl-3-dichlorofluoromethylthio-5a, 11b-dihydro-3H,5H,6H,4,7-dioxa-2,3-diazacyclopenta(c)phenanthrene; or 1,5,5-trimethyl-3-dichlorofluoromethylthio-5a,11b-dihydro-3H,5H,4-oxa-7-thia-2,3-diazacyclopenta(c)phenanthrene.

* * * * *

UNITED STATES PATENT AND TRADEMARK OFFICE
CERTIFICATE OF CORRECTION

PATENT NO. : 4,529,735
DATED : July 16, 1985
INVENTOR(S) : Engelbert Kühle, et al.

It is certified that error appears in the above-identified patent and that said Letters Patent is hereby corrected as shown below:

| | |
|---|---|
| Col. 1, line 45 | Delete "x" and substitute --X-- |
| Col. 1, line 46 | Delete "y" and substitute --Y-- |
| Col. 2, line 9 | Delete "present" and substitute --presence-- |
| Col. 2, line 58 | After "tert" delete "," and substitute --.-- |
| Col. 9, line 41 | Delete "solvents" and substitute --solvent-- |
| Col. 12, line 31 | After "compound" insert --according-- |
| Col. 12, line 33 and Col. 12, line 66 | After "5H," insert --6H,-- |
| Col. 12, line 59 | Correct "dichloro" |

Signed and Sealed this

Nineteenth Day of November 1985

[SEAL]

Attest:

DONALD J. QUIGG

Attesting Officer

Commissioner of Patents and Trademarks